United States Patent [19]

Barkhordar et al.

[11] Patent Number: 4,650,492

[45] Date of Patent: Mar. 17, 1987

[54] ARTIFICIAL HANDS

[75] Inventors: Mohammad Barkhordar; James M. Nightingale, both of Southampton; Denis R. W. May, Esher, all of United Kingdom

[73] Assignee: J. E. Hanger & Company Limited, London, England

[21] Appl. No.: 769,638

[22] Filed: Aug. 26, 1985

[30] Foreign Application Priority Data

Aug. 24, 1984 [GB] United Kingdom ............... 8421488

[51] Int. Cl.[4] .......................... A61F 1/00; A61F 1/06
[52] U.S. Cl. ...................................... 623/24; 901/33; 901/39; 250/231 P; 623/64
[58] Field of Search ...................................... 901/33–35, 901/31, 38, 39, 46, 47, 10; 128/77; 623/25, 63, 64, 24; 273/148 B; 250/231 P; 73/705

[56] References Cited

U.S. PATENT DOCUMENTS

| | | | |
|---|---|---|---|
| 3,418,661 | 12/1968 | Allison et al. | 901/38 |
| 3,751,733 | 8/1973 | Fletcher et al. | 901/33 |
| 3,904,234 | 9/1975 | Hill et al. | 250/231 P |
| 4,397,188 | 8/1983 | Bansevichus et al. | 901/10 |

Primary Examiner—Leo P. Picard
Assistant Examiner—MaryAnn Stoll Lastova
Attorney, Agent, or Firm—Pollock, VandeSande and Priddy

[57] ABSTRACT

An artificial hand comprises a palm member and thumb and finger members movable towards and away from one another by an actuator. A cosmesis covering the actuator has a touch sensor in a cavity of the cosmesis that deforms on contact with an object. The cavity is connected via a conduit with a microphone that picks up pressure waves resulting from stick/slip motion of the object along the surface of the cosmesis. The distance between the thumb and finger members is determined by a position sensor, and muscle sensor means responsive to contraction of first and second muscle groups supplies position and control signals in first and second channels. A controller operatively connected to the actuator is responsive to the presence and/or absence of signals in the first and second channels, the magnitudes of said channel signals when they are present, the presence and absence of contact signals from the touch sensor, the output of the position sensor, and the stick/slip signal from the microphone, to adjust the relative positions of the thumb and finger members.

7 Claims, 4 Drawing Figures

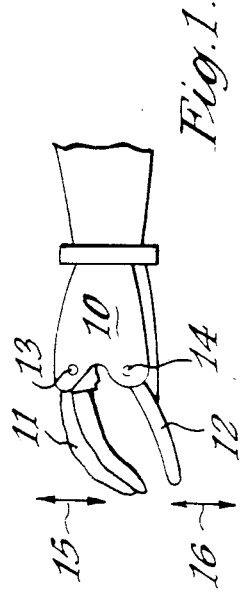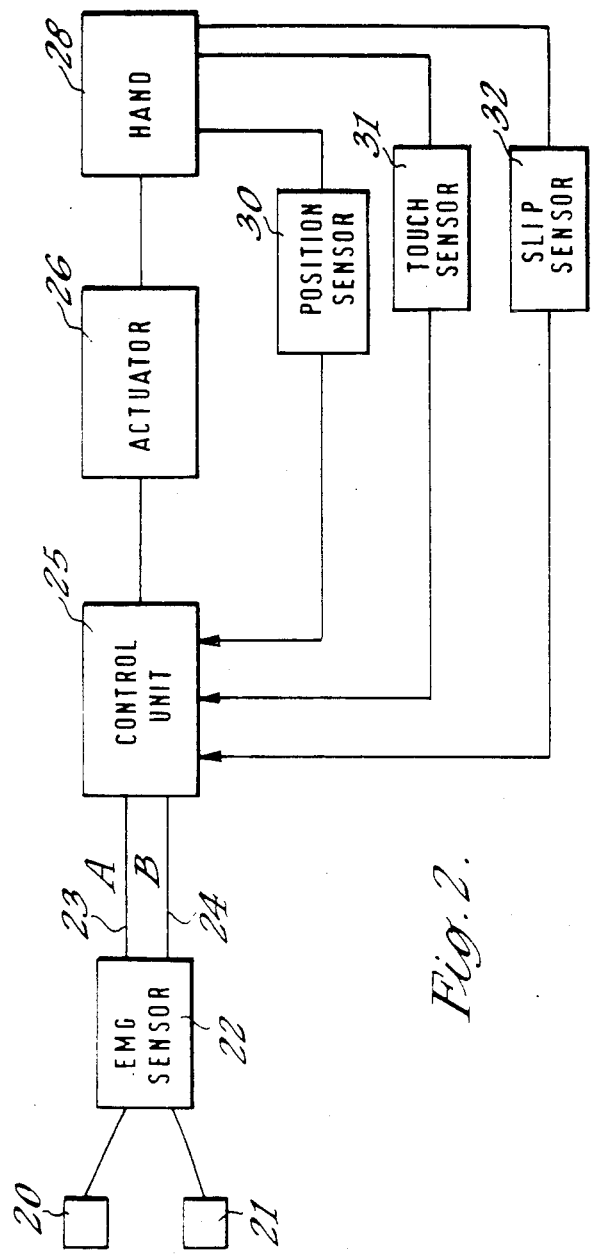

4,650,492

ARTIFICIAL HANDS

FIELD OF THE INVENTION

This invention relates to an electrically actuated artificial hand.

BACKGROUND TO THE INVENTION

Artificial hands having a single degree of freedom in which fingers and a thumb may be caused to approach and withdraw from each other by an electrical actuator are known and are supplied, for example, by Viennatone. Control circuits for such hands are described in Patent Specifications Nos. GB-A-1142417 and 1360933 and derive control signals derived from myoelectric currents that occur on contraction of a muscle or group of muscles to derive command signals for two control channels, one of which serves to open the hand and the other to close the hand. Although the fingers and thumb can be positioned with such mechanisms and wearers can pick up objects, these known mechanisms do not have any built-in response mechanism to alter their function when they contact an object to be picked up, nor do they allow the gripping force that they exert to be adjusted automatically to hold a fragile object without crushing it and to exert only that force that will prevent the object from slipping through the hand.

SUMMARY OF THE INVENTION

It is an object of the invention to provide an improved artificial hand and control apparatus that provides these additional functions.

It is a further object of the invention to provide a contact sensor that may be combined with a pressure sensor and a slip sensor and that may be buried in a cosmesis of foam rubber or like material forming a thumb or a finger cosmesis of a powered prosthetic hand and that is operable either to give an ON-OFF touch signal or to give a signal proportional to applied force.

Broadly stated the invention provides an artificial hand comprising a palm portion, a thumb portion and a finger portion supported by the palm portion for movement towards or away from one another, an actuator to move the thumb and finger portions towards one another to grip an object placed therebetween and away from one another to release said object, touch sensor means arranged to signal contact with said object, slip sensor means arranged to sense when said object gripped between said thumb and finger portions slips, muscle sensor means arranged to detect contraction of first and second muscle groups and supply position and grip command signals through respective control channels, position sensors means arranged to signal change in distance between the thumb and finger portions, and control means for the actuator that (a) responds to the position sensor to return the thumb and finger portions to a predetermined spacing corresponding to a parked position, (b) in the absence of a contact signal from the touch sensor means responds to the position command signal in the first control channel to alter the spacing between thumb and finger portions, (c) on a grip command signal in the second channel and on a contact signal from the touch sensor means responds to the signal from the slip sensor means to adjust the force exerted on said object through said thumb and finger portions by said actuator, and (d) on a release command signal opens the grip until the touch sensor means no longer gives a contact signal.

In a second aspect the invention provides a touch pressure sensor for an artificial hand comprising a light source and a light detector located in an enclosed cavity defined in a body of opaque resilient material forming a cosmesis of an artificial hand and arranged so that touch pressure on the hand adjacent the cavity deforms the cavity material to vary the proportion of the emitted light that is received by the detector in a manner that varies monotonically with applied load.

In a third aspect the invention provides a single cavity sensor buried in a deformable cosmesis of an artificial hand that provides a contact signal together with an acoustic signal for stick-slip motion of an object through the hand.

DESCRIPTION OF PREFERRED FEATURES

In the Viennatone type hand to which the invention is preferably applied the thumb portion and the finger portion are both hinged to said palm portion and are moved divergently by said actuator to open said grip and convergently to close said grip. The touch sensor means may include touch sensors on at least the thumb portion and the finger portion of the hand and, if desired, an additional touch sensor may be located in the palm portion of the hand. Each touch sensor may comprise a light source and a light detector within an enclosed cavity as aforesaid, combined with a load slip detector which is arranged to detect travel of the object in stick-slip motion, and which comprises a microphone, a conduit communicating the microphone with the cavity, and detector means selectively responsive to pressure waves resulting from the stick-slip motion.

The position sensor is preferably a Hall effect encoder on the shaft of a motor of the actuator connected to up/down counter means that stores the distance between the thumb and finger portions. The control means preferably maintains a closed parked position of the thumb and finger portions and opens the grip between thumb and finger portions on receipt of a command signal in the first control channel. Contraction of the second muscle group, preferably to give a myoelectric current above a predetermined threshold, preferably causes the state of the control means to be altered from grip positioning to object holding. Then contraction of the first muscle group to give a myoelectric current above another predetermined threshold may cause the state of the control means to alter from object holding to release.

The sensor may be used in association with control circuits that are adjustable for loss of sensitivity on application of another layer of material (e.g. a plastic cover layer) over the cosmesis. The sensor can be located near the surface of the cosmesis where it is most sensitive to applied load. It has the further advantage that it can "float" in the cosmesis and need not be rigidly connected to the endoskeleton of the hand. It may be combined with a load slip sensor for detecting travel of a load in stick-slip motion along a surface of a deformable material, said load slip sensor comprising a microphone, a conduit communicating the microphone with the aforesaid cavity, and detector means selectively responsive to pressure waves resulting from the stick-slip motion. It is a particular advantage of the above sensor that, by selective timing, a high response is obtainable to pressure waves from stickslip motion while a far lesser response occurs for ambient sound, e.g. speech or music or shock impact.

Advantageously, the cavity may be gas-tight, in which case a second conduit may lead to a pressure sensor operable to give a signal in response to a pressure rise in the cavity with applied load.

BRIEF DESCRIPTION OF THE DRAWINGS

An embodiment of the invention will now be described by way of example only with reference to the accompanying drawings, in which:

FIG. 1 is a diagrammatic view of the working parts of an endoskeletal artificial hand;

FIG. 2 is a block diagram of a control circuit for the artificial hand of FIG. 1;

DETAILED DESCRIPTION OF PREFERRED EMBODIMENTS

Figure 3:
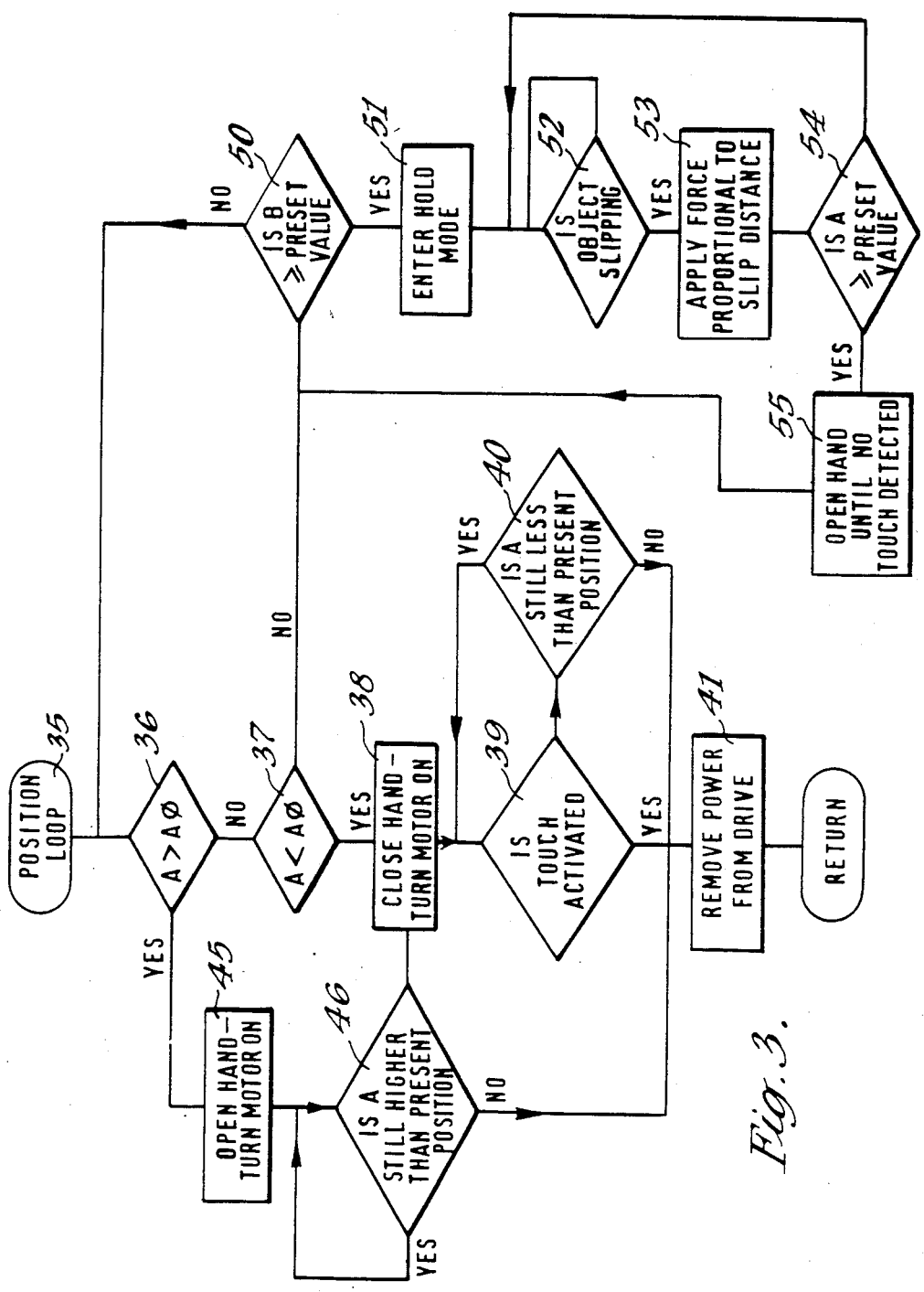
FIG. 3 is a flow chart indicating the sequence of operations performed by a control unit forming part of the circuit of FIG. 2.

In FIG. 1 an endoskeletal mechanism for an artificial hand comprises a palm portion 10, a finger portion 11 and a thumb portion 12 each pivoted to the palm portion 10 by pivots 13, 14. The thumb and finger portions 11, 12 are moved away from each other to open the grip and towards one another to close the grip by means of an electrically driven actuator within the palm portion 10 as indicated by arrows 15, 16. The mechanism of FIG. 1 is, of course, normally housed in a plastics cosmesis 100 (FIG. 4) simulating the shape of a natural hand.

The control system diagrammatically illustrated in FIG. 2 has two pairs of spaced electrodes 20, 21 to enable myoelectric sensor 22 to detect myoelectric currents that occur in two different muscle groups and supplies command outputs A and B in respective channels 23 and 24 to a control unit 25. The output of control unit 25 brings about movement of an actuator 26 of the hand 28 to open and close the grip between finger portion 11 and thumb portion 12. The motor of actuator 26 carries on its shaft a small bar magnet, and a pair of Hall effect devices are disposed at 90° about the shaft. Pulses from the Hall effect devices are fed to a logic unit that determines, from which of the detectors is leading, the direction in which the shaft is rotating and the output is fed via a Schmidt trigger to an up/down counter the stored value of which is significant of hand position. The above devices are indicated in FIG. 2 as position sensor 30, the output of which is fed to control unit 25. In the cosmesis 100 for the hand (FIG. 4) there are fitted touch sensor 31 and slip sensor 32 of the general kind illustrated in FIG. 4, both of which feed signals to the control unit 25.

The logic executed by the control unit is indicated in FIG. 3. The two pairs of surface electrodes 20, 21 are placed over flexor and extensor muscle groups in the forearm of a patient having a below-elbow prosthesis. A first command signal A is obtained as a differential signal of the EMG components and is used to select the appropriate grip function by comparison of the current value of A with the value $A\phi$ corresponding to the present hand position such that:

$A > A\phi$ ... open hand $A < A\phi$ ... closed hand

If the two muscles are contracted simultaneously and the two EMG components are added, a second command signal B can be derived by comparing the value of B with a predetermined threshold. The command signal B can be used to alter the control system from a positioning state to an autonomous article holding state in which conscious effort in the part of the patient is not required.

The control circuit 25 includes digital logic arranged to execute the sequence of instructions of FIG. 3. At step 35 it enters a position loop and tests at step 36 for the condition $A > A\phi$, and if the result is negative then at step 37 it tests for the condition $A < A\phi$. An affirmative answer at step 37 causes the control unit 25 to operate the motor of actuator 26 towards a parked position in which the grip is closed at step 38, and power is maintained until either the touch is activated at step 39 or the required position is reached at step 40, when power is removed from the motor at step 41 and the control unit returns to step 35. If $A > A\phi$ at step 36 the control unit branches to step 45 to operate the motor of actuator 26 in a hand opening direction, checks at step 46 for maintenance of the condition $A > A\phi$, and when $A < A\phi$ proceeds at step 41 to remove the drive to actuator 26.

If the result at step 37 is negative indicating that the hand has closed as required, the control unit 25 branches to step 50 and checks whether the value of command signal B from EMG sensor 22 is above the threshold. If the condition is satisfied, it enters a hold loop and proceeds at step 51 to enter the holding mode in which an article is autonomously gripped between finger portion 11 and thumb portion 12. It continuously checks at step 52 for a signal from slip sensor 32 and on an affirmative result applies at step 53 via actuator 26 a force proportional to a so-called "slip distance" which is derived by integrating the time for which a slip signal is present at sensor 32 so that the force applied by the finger portion 11 and thumb portion 12 is only that required to prevent the article from slipping. Release of the article is achieved when the signal A in channel 23 is above a preset value (which may be the maximum value thereof) and the control unit continuously tests at step 54 for this condition. If the result at step 54 is affirmative, the hand is opened at step 55 until the sensor 31 no longer indicates contact with an object, after which the control unit returns via step 50 to step 36 of the position loop.

It will be appreciated that by this sequence of operations the thumb and finger portions can be positioned under myoelectric control and the control circuit can be reversably changed from a positioning mode to an autonomous grip mode in which an article is gripped without the conscious control of the patient.

Figure 4:
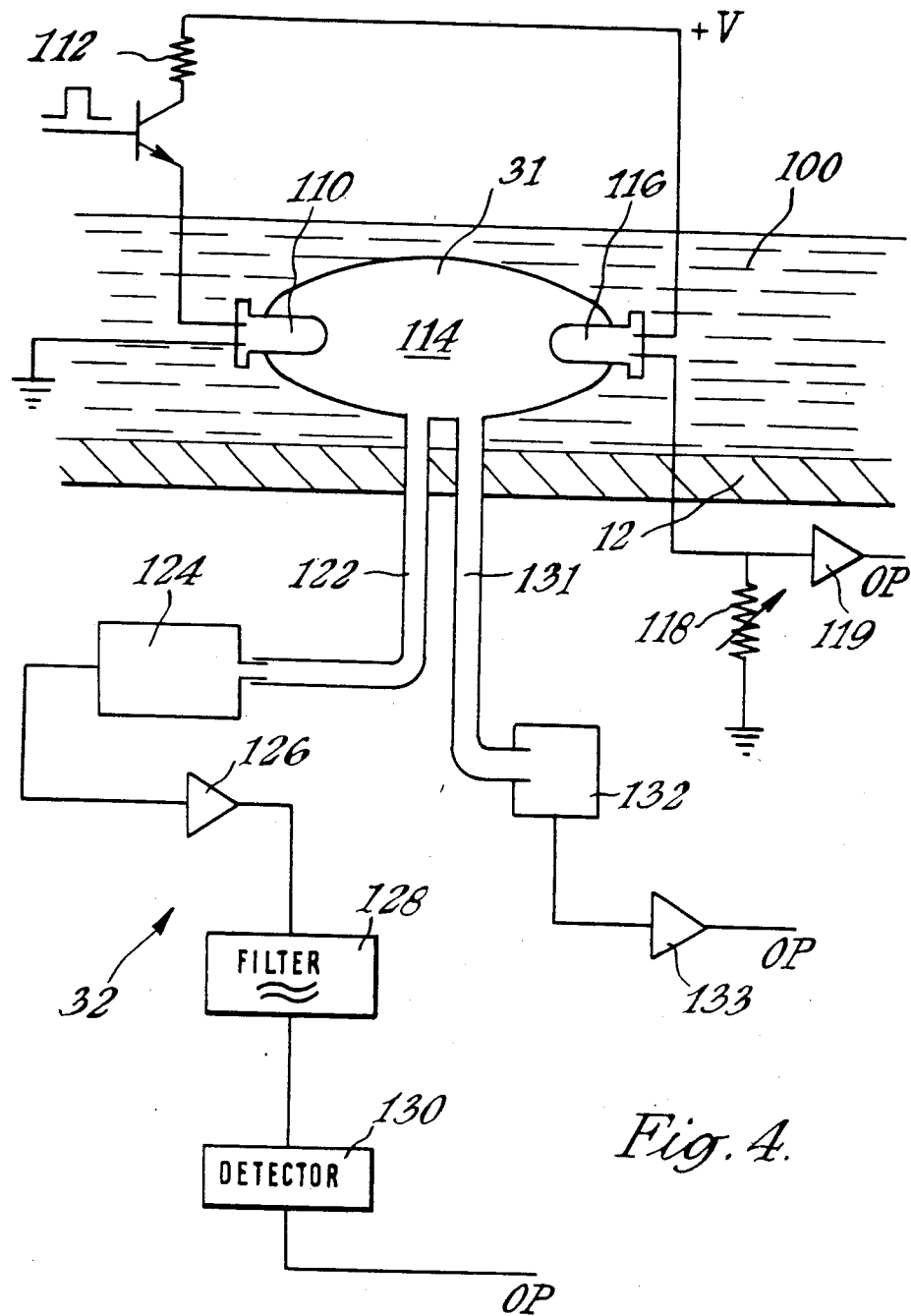
FIG. 4 is a description of a combined contact, stick-slip motion and pressure sensor buried in a cosmesis fitted over the endoskeletal structure of FIG. 1.

In FIG. 4 a combined contact pressure and stick-slip motion sensor is diagrammatically shown fitted to a region of elastomeric cosmesis 100 overlying thumb portion 12 of the artificial hand of FIG. 1. A light emitting diode 110 powered via resistor 112 provides a continuous light output and is located to one side of a gas-containing cavity 114 within the otherwise light opaque resilient cosmesis 100. To the other side of the cavity 114 is provided phototransistor 116 that receives light reflected from walls of the cavity and direct light from the diode 110, and in the rest state phototransistor 116 will provide a constant voltage when the power to diode 110 remains unchanged. But when a load is applied to cosmesis 100 having a component orthogonal to the light beam, the cavity 114 is compressed to a degree depending upon the mechanical properties of the surrounding resilient material and also on the increased pressure of the gas entrapped in the cavity. The result is to vary the voltage output of phototransistor 116 in monotonic relationship to the applied load.

The voltage output is derived by potentiometer or resistor 118 and may be amplified by amplifier 119 and then applied to a potentiometer or an A/D converter for digitization. The ambient output value may be compared with a known rest value which may be set to zero by varying the value of potentiometer 118, a change from the rest value denoting contact of the material about the sensor with an object.

The path between the light emitter 110 and detector 116 need not be straight, but can be generally arcuate, light being transmitted by internal reflection. It is also to be understood that the light source 110 need not be operated continuously but may be pulsed by the action of a control circuit with a minimum duration and frequency dependant on the particular light emitters and detector used.

From the same cavity 114 a conduit 122 leads to a microphone 124 connected via amplifier 126 to an appropriate filter 128 and detector 130. The filter 128 selectively passes frequencies associated with stick-slip motion of different textured objects, e.g. to be gripped by the prosthetic hand, and the detector 130 detects the onset or cessation of slip as signals occuring above a defined threshold. The fact that the cavity 114 is wholly within the resilient material means that it selectively collects vibrations transmitted within the resilient material and attenuates external vibrations.

Also, connected to the cavity 114 via tube 131 is a pressure sensor 132 responsive to changes in gas pressure in cavity 114 due to applied load. The signal from sensor 132 is amplified by amplifier 133 and digitized. By this means large forces may be detected while the optical sensor 110, 116 detects very low contact forces.

It will be appreciated that various modifications may be made to the embodiment described above without departing from the invention the scope of which is defined in the appended claims.

We claim:

1. An artificial hand comprising in combination:
   a palm member, thumb and finger members supported by said palm member, and a cosmesis covering said palm, thumb and finger members;
   an actuator operably connected to at least one of said thumb and finger members for moving said thumb and finger members towards one another to grip an object placed therebetween, and for moving said thumb and finger members away from one another to release said object;
   touch sensor means operative to signal contact with said object, said touch sensor means consisting of at least one sensor which comprises an enclosed cavity defined by portions of said cosmesis, and a light source and a light detector within said cavity, portions of said cavity between said light source and said detector being deformable on contact with the object to provide said contact signal by reduction of the light that is transmitted between said light source and said detector;
   a load slip sensor for sensing when the object gripped between said thumb and finger members slips, said load slip sensor comprising a microphone in said cosmesis, a conduit in said cosmesis connecting said microphone with said cavity, and detector means coupled to said microphone and selectively responsive to pressure waves resulting from stick-/slip motion of said object along the surface of said cosmesis to provide a signal when the object slips;
   muscle sensor means arranged to detect contraction of first and second muscle groups and to supply position and grip command signals through first and second control channels;
   a position sensor arranged to signal change in distance between said thumb and finger members; and
   control means for the actuator, said control means being (a) in a first state, in the absence of signals in the first and second control channels, where it responds to said position sensor to maintain a parked position of said thumb and finger members, (b) in a second state, in the presence of a signal in the first control channel and in the absence of a contact signal from said touch sensor means, where the actuator is caused to alter the spacing between said thumb and finger members in response to said signal in said first control channel, (c) in a third state, upon occurrence of a signal above a predetermined threshold in the second control channel and the presence of a contact signal from the touch sensor means, where a force exerted on said object by said actuator through said thumb and finger members is increased in response to the signal from said load slip sensor until the object no longer slips, and (d) in a fourth state, in response to a signal in the first channel above a predetermined threshold, where the actuator moves said thumb and finger members apart until said touch sensor means no longer gives a contact signal.

2. An artificial hand according to claim 1 wherein said muscle sensor means includes means responsive to contraction of the second muscle group resulting in a myoelectric current above a predetermined threshold to cause the control means to be altered from its second to its third states.

3. An artificial hand according to claim 2 wherein said muscle sensor means includes means responsive to contraction of the first muscle group resulting in a myoelectric current above a predetermined threshold to cause the control means to alter from its third to its fourth state.

4. An artificial hand according to claim 1, wherein the touch sensor means includes touch sensors on at least said thumb member and said finger member of said hand.

5. An artificial hand according to claim 1, wherein the position sensor is a Hall effect encoder on the shaft of a motor of the actuator connected to up/down counter means that stores the distance between the thumb and finger members.

6. An artificial hand according to claim 1, wherein the light source is a light (including infra red) emitting diode and the light detector is a phototransistor.

7. An artificial hand according to claim 1, wherein said cavity is gas-tight and a second conduit leads to pressure sensor means operative to give a signal in response to the pressure in said cavity.

* * * * *